United States Patent [19]

Harris

[11] Patent Number: 5,229,380
[45] Date of Patent: Jul. 20, 1993

[54] **METHOD FOR TREATING *HELICOBACTER PYLORI* GASTRITIS**

[76] Inventor: Richard Y. Harris, 381 Rampart Range Rd., Woodland Park, Colo. 80863

[21] Appl. No.: 724,529

[22] Filed: Jun. 28, 1991

[51] Int. Cl.$^5$ ............................................. A61K 31/65
[52] U.S. Cl. ................................... 514/152; 514/926; 514/927
[58] Field of Search ....................... 514/152, 926, 927

[56] References Cited

PUBLICATIONS

Compendium of Drug Therapy, pp. 25:6–7, (1983–1984), Biomedical Information Corp., Publishers.
Chemical Abstracts, 112(5):135883(s), Magalhaes et al. (1989).
Warren, et al., "Unidentified Curved Bacilli on Gastric Epithelium in Active Chronic Gastritis," Lancet, vol. 1, 1983—pp. 1273–1275.
Marshall, et al., "Unidentified Curved Bacilli in the Stomach of Patients With Gastritis and Peptic Ulceration," Lancet, vol. 1, 1984—pp. 1311–1315.
Langenberg, et al., "The Pathogenic Role of *Campylobacter Pyloris* Studied by Attempts to Eliminate these Organisms," Abst. 98 in Proc. of the Third Int'l Workshop on Campylobacter Infections, Pearson, et al., eds., Public Health Laboratory Service, 1985—pp. 162–163.
Czinn and Speck, "*Campylobacter pylori*: A New Pathogen," J. Peds, vol. 144, 1989—pp. 670–672.

*Primary Examiner*—Frederick E. Waddell
*Assistant Examiner*—Raymond J. Henley, III
*Attorney, Agent, or Firm*—Kenyon & Kenyon

[57] ABSTRACT

The invention relates to a method of arresting and treating duodenal and gastric ulcers, and chronic gastritis comprising administering an effective amount of [4S(4α,4aα,5aα,12aα)]-4,7-bis (dimethylamino)-1,4,4a,5,5a,6,11,12a-octahydro-3,10,12, 2a-tetrahydroxy-1,11-dioxo-2-napthacenecarboxymide monohydrochloride.

16 Claims, No Drawings

METHOD FOR TREATING *HELICOBACTER PYLORI* GASTRITIS

FIELD OF THE INVENTION

This invention relates to a method for arresting and treating duodenal and gastric ulcers, and chronic gastritis, and more particularly the use of the compound [4S-(4α,4aα,5aα,12aα)]-4,7-bis (dimethylamino)-1,4,4a,5,5a,6,11,12a-octahydro-3,10,12,12a-tetrahydroxy-1,11-dioxo-2-napthacenecarboxymide monohydrochloride, commonly known as minocycline, to eradicate the bacterium *Helicobacter pylori* (previously named *Campylobacter pylori*), which is believed to play an etiologic role in these disorders.

BACKGROUND OF THE INVENTION

Patients suffering ulcer-like or hyperacidity symptoms may be treated by established anti-ulcer drugs like Tagamet ® (cimetidine) or Zantac ® (ranitidine hydrochloride), which slow down the rate of acid secretion by the stomach. Patients maintained on the standard anti-ulcer drug regimen for one week generally exhibit a fairly rapid and favorable response, but unless continuously administered, patients soon suffer recurrences of their symptoms. Patients may also be treated with liquid or tablet antacid agents which coat the lining of the stomach and/or reduce acidity. These regimens are merely palliative. In advanced cases, surgery may be required.

For some time now, it has been speculated that the bacterium *Helicobacter pylori* plays an etiologic role in the development of both duodenal and gastric ulcers, and in chronic gastritis. Specifically, some Australian researchers have hypothesized that the *Helicobacter pylori* microorganism lives and grows between the inner lining of the stomach and under the protective mucous coat which protects the stomach lining from the corrosive effects of stomach acid. See Lancet. 1983; Vol. 1, pages 1273-5; Lancet. 1984; Vol. 1, pages 1311-5.

Bacteria in the stomach are typically killed by acid secreted by the cells lining the stomach. Similarly, with *Helicobacter pylori*, the stomach lining senses that the *Helicobacter pylori* bacteria are present and causing infection. In response, the stomach lining cells increase their production of stomach acid to try and kill the *Helicobacter pylori* bacteria. The area between the mucous coat and the stomach inner lining inhabited by the *Helicobacter pylori* is, however, a difficult area for the acids to penetrate because of the overlying protective stomach mucous coating.

Consequently, the acid produced in response to the bacteria flows downstream from the stomach and may cause gastric or duodenal ulcers. It is also possible that areas of the stomach directly infected by the *Helicobacter pylori* bacteria also develop ulcerations.

Research studies have established a link between the presence of chronic antral gastritis, and gastric and duodenal ulcers, and *Helicobacter pylori* gastric infection. Seventy to eighty-five percent of biopsy specimens from patients with chronic gastritis test positive for this organism.

Attempts to treat the organism with known regimens have proved ineffective, however. In 1985, Langenberg et al. reported attempts to eliminate the *Helicobacter pylori* organism from the inner stomach lining. Administration of bismuth to infected patients was found to result in diminution of symptoms, and endoscopic examinations did not detect the presence of *Helicobacter pylori* organisms in eleven of eighteen patients maintained on bismuth for up to eight weeks. The antibiotic amoxicillin was found to reduce the number of *Helicobacter* gastric organisms in seven of eight patients treated for four weeks. However, three each of the bismuth and amoxicillin treated patients were found to have *Helicobacter pylori* organisms on the inner stomach lining after being studied four to thirteen weeks following completion of their therapies. Subsequent bacterial infection with another strain of *Helicobacter pylori* was eliminated as a possibility. Langenberg, Rauws, et al. The pathogenic role of *Campylobacter pylori* studies by attempts to eliminate these organisms. Abstract 98 in Proceedings of the Third International Workshop on *Campylobacter* Infections. Pearson et al, eds. Public Health Laboratory Service. 1985; 165-66.

Experiments with other antibiotics, such as tinidazole and doxycycline in conjunction with bismuth were similarly ineffective.

In fact, studies have shown that a majority of patients who showed negative endoscopic cultures for *Helicobacter pylori* at the completion of standard antibiotic treatments were found to have positive *Helicobacter pylori* cultures within four weeks after finishing treatment. Thus, it appears that these patients had their *Helicobacter pylori* infections suppressed by the treatments without eradication of the offending organism. While various anti-bacterial regimens are more successful in treating chronic gastritis and gastric and duodenal ulcers than palliative regimens only, the known antibacterial treatments used in the various studies have thus far failed to result in reliable high rates of eradication of *Helicobacter pylori* lasting more than four weeks.

The failure of antibiotics thus far to reliably eradicate the *Helicobacter pylori* organism may be due to the inability of most orally administered antibiotics to adequately penetrate the space between the inner stomach lining and the stomach protective mucous layer. This failure would explain the antibiotic suppression, but not eradication, of *Helicobacter pylori* organisms.

In fact, investigators have noted that the use of common antibiotics to treat gastric *Helicobacter pylori* infections is associated with an eventual almost one hundred percent relapse rate. Czinn and Speck. *Campylobacter pylori*: a new pathogen. J. Peds. 1989; 144:670-672.

Thus, as with known regimens, the antibiotic and chemical treatments are merely palliative. It would be desirable then to find an antibiotic which is able to penetrate the space under the gastric mucous layer in an amount effective to produce more successful treatment of *Helicobacter pylori* infections.

ADVANTAGES AND SUMMARY OF THE INVENTION

An advantage of the present invention is to provide a novel and effective treatment for both duodenal and gastric ulcers, and chronic gastritis, associated with the presence of *Helicobacter pylori*.

Another advantage of the present invention is to provide a method for treating *Helicobacter pylori* infections which is longer lasting and more cost effective than known treatment modalities.

The present invention provides a method for arresting and treating duodenal and gastric ulcers, and chronic gastritis which comprises administering an effective amount of [4S-(4α,4aα,5aα,12aα)]-4,7-bis (dimethylamino)-1,4,4a,5,5a,6,11,12a-octahydro-3,10,12,12a-tetrahydroxy-1,11-dioxo-2-napthacenecarboxymide monohydrochloride.

The present invention also provides a method for treating Helicobacter pylori bacterial infections of the stomach lining comprising orally administering an effective amount of [4S-(4α,4aα,5aα,12aα)]-4,7-bis (dimethylamino)1,4,4a,5,5a,6,11,12a-octahydro-3,10,12,12a-tetrahydroxy-1,11-dioxo-2-napthacenecarboxymide monohydrochloride.

The present invention further provides a method for treating gastric disorders such as duodenal ulcers with an effective amount of [4S-(4α,4aα,5aα,12aα)]-4,7-bis (dimethylamino)-1,4,4a,5,5a,6,11,12a -octahydro-3,10,12,12a-tetrahydroxy-1,11-dioxo-2-napthacenecarboxymide monohydrochloride.

The present invention further provides a method for treating gastric disorders such as peptic ulcers with an effective amount of [4S-(4α,4aα,5aα,12aα)]-4,7-bis (dimethylamino)-1,4,4a,5,5a,6,11,12a-octahydro-3,10,12,12a-tetrahydroxy 1,11-dioxo-2-napthacenecarboxymide monohydrochloride.

The present invention further provides a method for treating gastric disorders such as chronic gastritis with an effective amount of [4S-(4α,4aα,5aα,12aα)]-4,7-bis (dimethylamino)-1,4,4a,5,5a,6,11,12a-octahydro-3,10,12,12a-tetrahydroxy-1,11-dioxo-2-napthacenecarboxymide monohydrochloride.

The present invention further provides a method for controlling Helicobacter pylori in the alimentary canal by treating said canal with an effective amount of [4S-(4α,4aα,5aα,12aα)]-4,7-bis (dimethylamino)-1,4,4a,5,,5a,6,11,12a-octahydro-3,10,12,12a-tetrahydroxy-1,11-dioxo-2napthacenecarboxymide monohydrochloride.

The following clinical tests further illustrate the present invention but are not construed to limit the scope thereof.

PROTOCOL OF CLINICAL TESTS

Minocycline, (such as Minocin ® tablets or capsules available in dosages of 50 mg or 100 mg or as oral suspension in 50 mg dosages from Lederle Laboratories, Pearl River, N.J. 10965, described in the Physicians' Desk Reference, pages 1169–70, 44th ed., 1990) was administered orally to 42 patients with symptoms typical of gastric and duodenal ulcers and chronic gastritis. Twenty-seven of the patients were initially treated for one week, following a standard regimen, with an established anti-ulcer drug such as Tagamet ® or Zantac ®. As the response to these anti-ulcer drugs is usually fairly rapid and dramatic, reduction of ulcer symptoms in response to Tagamet ® or Zantac ® was used to confirm the clinical suspicion that either chronic gastritis, gastric ulcer, or duodenal ulcer was present. Prior to commencement of minocycline therapy, the anti-ulcer drug regimen was stopped.

TEST 1

Thirteen patients received minocycline orally, 50 mg, four times daily, for three weeks. Seven of the patients had a final diagnosis of Helicobacter pylori infection only, uncomplicated by the co-existence of problems such as reflux esophagitis or symptomatic hiatus hernia. Nine of the patients had complete resolution of their upper gastrointestinal symptoms initially. When examined four weeks after cessation of minocycline therapy, eight of the nine patients had no recurrence of symptoms and exhibited normal bowel sounds, in contrast to the low intensity hyperactive bowel sounds associated with Helicobacter pylori gastric infections, and no upper abdominal tenderness. Of the eight patients with no recurrence of symptoms, six had Helicobacter pylori infection only. Thus, three weeks of therapy appears to be effective in eliminating uncomplicated Helicobacter pylori infection in 75% of patients with a diagnosis of this infection only, notwithstanding a high failure rate with known regimens.

TEST 2

Twenty patients received minocycline orally, 50 mg four times daily, for two weeks. Fourteen of the patients had a final diagnosis of Helicobacter pylori infection only, uncomplicated by the co-existence of problems such as reflux esophagitis or symptomatic hiatus hernia. Seventeen of the patients had complete resolution of their upper gastrointestinal symptoms initially. When examined four weeks after cessation of minocycline therapy, 15 of the 17 patients had experienced no recurrence of symptoms. Of those 15 patients, 14 had Helicobacter pylori infection only. Thus, two weeks of therapy appears to be effective in eliminating uncomplicated Helicobacter pylori infection in 100% of patients who had infection only.

TEST 3

Nine patients received minocycline orally, 50 mg, four times daily, for one week. Seven of the patients had a final diagnosis of Helicobacter pylori infection only, uncomplicated by the co-existence of problems such as reflux esophagitis or symptomatic hiatus hernia. Six of the patients initially had complete resolution of the upper gastrointestinal symptoms. When examined four weeks after cessation of minocycline therapy, four of the six patients had experienced no recurrence of symptoms. All four had Helicobacter pylori infection only. Thus, one week of therapy appears to have effectively eliminated uncomplicated Helicobacter pylori infection in 57% of patients who had infection only.

RESULTS

Twenty-eight patients who had Helicobacter pylori infection only, without concurrent reflux esophagitis or hiatus hernia, were treated with oral minocycline for periods ranging from one to three weeks. When examined four weeks after cessation of therapy, 24 of the 28 patients were symptom free, yielding a success rate of 85.7%. Of the 21 patients who were treated with oral minocycline for at least two weeks, 19 or 90.4% were symptom free four weeks after cessation of therapy. As seen from these results, the method of the present invention of orally administering minocycline appears to have substantially reduced Helicobacter pylori infection and its symptoms for at least four weeks.

Follow-up evaluation of 15 of the 24 patients (9 were lost to follow-up) showed that all patients remained free of the original gastrointestinal symptoms for an average of 19.1 months. The maximum time of freedom from symptoms for these 15 patients was 30 months and the minimum time was 11 months.

Eight of the 15 patients had received a course of oral H2 antagonist, e.g., Tagamet ® or Zantac ®, prior to starting minocycline therapy. The remaining seven patients did not receive any H2 antagonist. As noted above, the outcomes were the same. Thus, the prior use of an H2 antagonist appears to have no effect on the long term efficacy of minocycline.

In contrast to the results observed in the above tests, 15 patients who received treatment with minocycline had a relapse within four weeks of cessation of therapy and included: eight patients who did not, on final diagnosis, have *Helicobacter pylori* infection; three patients who had reflux esophagitis or hiatus hernia in addition to *Helicobacter pylori*; three patients who had been treated with minocycline for one week only; and one patient who had a final diagnosis of *Helicobacter pylori* only and had been treated with minocycline for at least two weeks.

Thus, after a course of treatment with oral minocycline there is a remarkable and long lasting eradication of gastric symptoms when oral minocycline is administered for at least two weeks to patients without concurrent upper intestinal disease unrelated to *Helicobacter pylori* gastritis, but which exhibits similar symptoms.

TEST 4

A patient with symptoms of a bleeding gastric ulcer was treated with Tagamet ® for six weeks. The patient was then examined with a fiberoptic gastroscope in order to evaluate the inner lining of the esophagus, stomach, and duodenum. The patient was shown to have a healing gastric ulcer. A culture taken at that time showed *Helicobacter pylori* from the base of his ulcer.

Tagamet ® was stopped and the patient was then treated with minocycline for two weeks. The patient still had some symptoms at the time the minocycline was started, but after two weeks treatment with minocycline, the patient's symptoms completely resolved. There has been no recurrence of ulcer symptoms or bleeding 23 months after the patient was treated with minocycline. Thus, oral minocycline appears to be a highly effective treatment for uncomplicated *Helicobacter pylori* gastritis.

Accordingly, the present invention provides a method for arresting and treating duodenal and gastric ulcers, and chronic gastritis by treatment with the antibiotic minocycline.

I claim:

1. A method for treating gastrointestinal disorders associated with *Helicobacter pylori* which comprises administering an effective amount of a compound 4,7-bis (dimethylamino)-1,4,4a,5,5a,6,11,12a-octahydro-3,10,12,12a-tetrahydroxy-1,11-dioxo-2-naphthacenecarboxamide to a patient in need thereof.

2. The method as recited in claim 1, wherein said gastrointestinal disorder is duodenal ulcers.

3. The method as recited in claim 1, wherein said gastrointestinal disorder is peptic ulcers.

4. The method as recited in claim 1, wherein said gastrointestinal disorder is chronic gastritis.

5. The method as recited in claim 1 wherein said compound penetrates a space between the inner stomach lining and 6. A method for treating *Helicobacter pylori* infections of the alimentary canal comprising orally administering an effective amount of the compound 4,7-bis (dimethylamino)-1,4,4a,5,5a,6,11,12a-octahydro-3,10,12,12a-tetrahydroxy-1,11-dioxo-2-naphthacenecarboxamide to a patient in need thereof.

7. The method as recited in claim 6 wherein the amount of compound ranges from 100 mg to 600 mg daily.

8. The method as recited in claim 6 wherein the amount of compound administered is 50 mg, four times daily, for three weeks.

9. The method as recited in claim 6 wherein the amount of compound administered is 50 mg, four times daily, for two weeks.

10. The method as recited in claim 6 wherein the amount of compound administered is 50 mg, four times daily, for one week.

11. The method as recited in claim 6 wherein the amount of compound administered is 50 mg, two times daily for one week.

12. The method as recited in claim 6 wherein the amount of compound administered is 50 mg, two times daily for two weeks.

13. The method as recited in claim 6 wherein the amount of compound administered is 50 mg, two times daily for three weeks.

14. The method as recited in claim 6 wherein the amount of compound administered is 50 mg, six times daily for one week.

15. The method as recited in claim 6 wherein the amount of compound administered is 50 mg, six times daily for two weeks.

16. The method as recited in claim 6 wherein the amount of compound administered is 50 mg, six times daily for three weeks.

* * * * *